(12) United States Patent
Laurent et al.

(10) Patent No.: US 7,396,995 B2
(45) Date of Patent: Jul. 8, 2008

(54) CONNECTOR

(75) Inventors: Kristopher Poh Ming Laurent, London (GB); Alastair Edwin McAuley, Auckland (NZ); Christopher Earl Nightingale, London (GB); Ian Douglas Makinson, Auckland (NZ); Ivan Milivojevic, London (GB); Grant Warren Wilson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/572,535

(22) PCT Filed: Aug. 20, 2004

(86) PCT No.: PCT/NZ2004/000195

§ 371 (c)(1),
(2), (4) Date: Oct. 23, 2006

(87) PCT Pub. No.: WO2005/028012

PCT Pub. Date: Mar. 31, 2005

(65) Prior Publication Data

US 2007/0079982 A1    Apr. 12, 2007

(30) Foreign Application Priority Data

Sep. 19, 2003  (NZ) .................................. 528390

(51) Int. Cl.
*H01H 9/02*    (2006.01)
(52) U.S. Cl. ................ 174/53; 174/48; 52/28; 439/191

(58) Field of Classification Search .............. 174/53, 174/48; 52/28; 128/203.17, 204.17; 261/107, 261/129; 439/191–195, 350–358
See application file for complete search history.

(56) References Cited

U.S. PATENT DOCUMENTS

| 4,901,719 | A |  | 2/1990 | Trenconsky et al. |
| 5,392,770 | A |  | 2/1995 | Clawson et al. |
| 5,537,996 | A |  | 7/1996 | McPhee |
| 5,980,289 | A |  | 11/1999 | Engle |
| 6,105,572 | A | * | 8/2000 | Shaffer et al. .......... 128/200.24 |
| 6,783,379 | B2 | * | 8/2004 | Kerscher et al. ............ 439/191 |
| 6,953,354 | B2 |  | 10/2005 | Edirisuriya et al. |
| 7,059,881 | B2 | * | 6/2006 | Song et al. .................. 439/191 |
| 7,146,979 | B2 | * | 12/2006 | Seakins et al. ......... 128/203.17 |
| 7,192,295 | B1 | * | 3/2007 | Yeh et al. .................... 439/350 |
| 7,223,917 | B1 | * | 5/2007 | Marszalek et al. ........ 174/84 R |
| 7,227,081 | B2 | * | 6/2007 | Bally et al. ................... 174/53 |

FOREIGN PATENT DOCUMENTS

DE       3110903       9/1982

* cited by examiner

*Primary Examiner*—Dhiru R Patel
(74) *Attorney, Agent, or Firm*—Trexler, Bushnell, Giangiorgi, Blackstone & Marr, Ltd.

(57) ABSTRACT

A connector (20) to a couple breathing conduit to a patient interface or another conduit. The connector allows for an electrical connection (22a, 22b) in a first conduit (14a) to be connected to another electrical connection (21a, 21b) in a patient interface or second conduit (14b). The connector is capable of swivelling without disrupting the gas flow through the conduits of the electrical connection.

4 Claims, 6 Drawing Sheets

CONNECTOR

BACKGROUND TO THE INVENTION

1. Field of the Invention

The present invention relates particularly, though not solely, to the delivery of humidified pressurised oxygen and/or air to a patient. In particular, the present invention relates to connections used to couple heated breathing conduits together.

2. Summary of the Prior Art

In order to supply gases to a patient or a person needing such gases, it may sometimes be necessary to first humidify those gases, for example using a respiratory humidifier/ventilator system. In such a case where the gases have been humidified, and therefore laden with water, it is likely that during transport through a conduit to the patient, condensation of that water vapour will occur. In order to overcome this disadvantage it is known to associate a heater wire with respiratory humidifier breathing conduits to avoid condensation. Examples of such a heated breathing conduit are disclosed in U.S. Pat. No. 5,537,996 (McPhee) and U.S. Pat. No. 5,392,770 (Clawson et al.).

A piece of soft extremely flexible connecting tube is commonly used at the end of a heated respiratory conduit to connect to a mask or mouthpiece. The breathing circuit, while flexible, will necessarily be stiff enough to maintain its integrity over comparatively long runs, while the connecting tube, being only a short length, for example 10 centimetres, merely has to span between the user's mouth and chest, and can thereby be made in a manner that would not be suitable for long runs. It has been found that condensation may form in the short flexible connecting tube causing problems to the patient.

SUMMARY OF THE INVENTION

It is an object of the present invention to provide a tubing connector between heated breathing conduits and/or patient interfaces that goes some way towards overcoming the above-mentioned disadvantages.

Accordingly, in a first aspect the present invention consists in a connector to couple a first conduit to a second conduit, where said first conduit includes at least one elongate electrical means extending within, through out or about it, and said second conduit includes at least one electrical means extending within, throughout or about it, said connector comprising:

a male portion of a generally tubular shape connected to one end of said first and said second conduit, said male portion having one or more electrical contact means on the exterior of said male portion, a female portion of a generally tubular shape connected to one end of the other said first conduit and said second conduit, said female portion having one or more electrical contact receiving means on the interior of said female portion, wherein coupling of said male and said female portions causes said electrical contact means to engage with said electrical receiving means, said coupling simultaneously causing a gaseous and electrical connection between said first conduit and one second conduit, and said coupling being able to be swivelled or twisted without disrupting said gaseous and electrical connection.

Preferably said elongate electrical means and said electrical means are heating elements means to heat said first conduit and second conduit.

Alternatively said elongate electrical means and said electrical means are wires that provide power to or enable sensing at said patient interface connected to at least one of said first or second conduits.

Alternatively said elongate electrical means and said electrical means include both a heating element means to heat at least one of said first and second conduits and a wire to supply power to at least one of said first and second conduits.

Preferably said gases supply means is a humidifier.

Alternatively said gases supply means is an integrated blower and humidifier.

Alternatively said gases supply means is a positive pressure ventilation device.

Preferably said electrical contact means and said electrical contact receiving means are made from electrically conductive material.

BRIEF DESCRIPTION OF THE DRAWINGS

One preferred form of the present invention will now be described with reference to the accompanying drawings.

DETAILED DESCRIPTION OF THE PREFERRED EMBODIMENTS

The present invention provides improvements in the field of CPAP therapy. In particular to a connector that creates both an electrical and a gaseous connection between two conduits. This connection has the advantage of being able to be twisted and swivelled without loss of electrical or gaseous connection between the two conduits. It will be appreciated that the connector as described in the preferred embodiment of the present invention can be used in respiratory care generally or with a ventilator, but will now be described below with reference to use in a humidified CPAP system. It will also be appreciated that the connector is equally applicable to all forms of patient interface.

Figure 1:
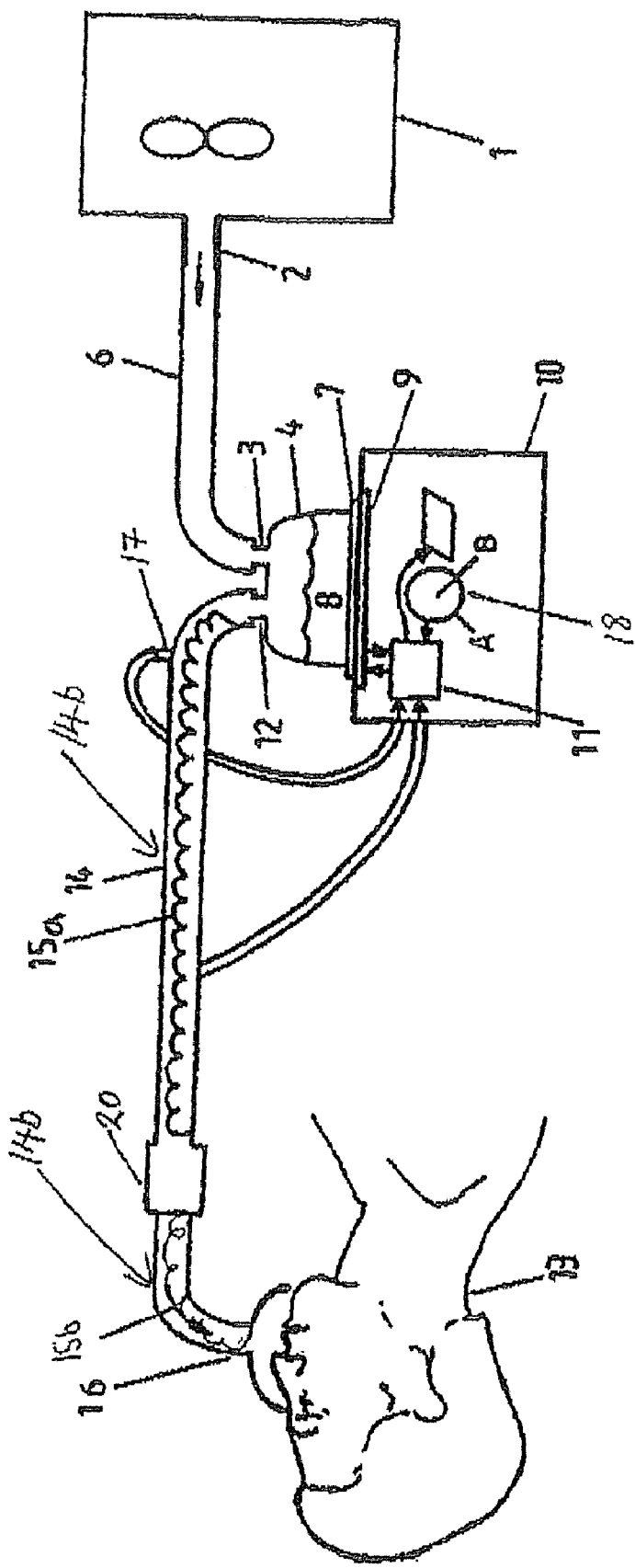
FIG. 1 is an illustration of a humidified continuous positive airway pressure (CPAP) system as might be used in conjunction with the connector of the present invention.

With reference to the accompanying drawings and in particular to FIG. 1, an example of humidification apparatus and respiratory humidification system incorporating preferred embodiments of the connector of the present invention is illustrated. In the description below, reference has been made to the connection of a breathing conduit to another breathing conduit, it must be appreciated that the connector of the present invention may be used in medical devices, for example, a positive pressure ventilation devices, continuous positive airway pressure (CPAP) devices, insufflation devices, integrated insufflation and humidification devices, integrated CPAP and humidifier devices, or any other such breathing assistance device that can be used in either homecare or hospital applications. The use of the word humidifier alone must not be seen as restrictive to the application or use of the connector of the present invention.

Included in the example respiratory humidification system as shown in FIG. 1, is a gases supply means 1, such as a ventilator or blower, having an outlet 2 that supplies gases (for example oxygen, anaesthetic gases or air) to the inlet 3 of a humidification chamber means 4 via a conduit 6. The humidification chamber means 4 may, for example, comprise a plastics formed chamber having a metal base 7 sealed thereto. The humidification chamber 4 is adapted to hold a volume of water 8, which is heated by a heater plate means 9 under the control of controller or control means 11 of a humidification device or humidifier 10.

As the water within chamber 4 is heated it will slowly evaporate, mixing water vapour with the gases flow through the humidification chamber from ventilator 1. Accordingly, humidified gases leave the humidification chamber 4 via outlet 12 and are passed to a patient or other person in need of such gases 13 through a gases transportation pathway or inspiratory conduit 14. In order to reduce condensation within the inspiratory conduit 14 and to raise the temperature of the gases provided to the patient 13 heating element 15a is provided which is energised under the control of control means 11. The inspiratoly conduit 14 is comprised of two sections a stiff section 14a containing heating element 15a and a flexible section 14b which contains a heating element 15b. The sections 14a and 14b are connected together by the connector 20 of the present invention.

The gases outlet 12 on the humidifying chamber 21 is provided and conduit 14, conveys humidified gases to the patient at the end 16 of the conduit. The end 16 of the conduit may have a cannula connected to the patients nose, nasal mask or face mask connected to the user's face, so as to supply humidified gases to the user.

Figure 2:
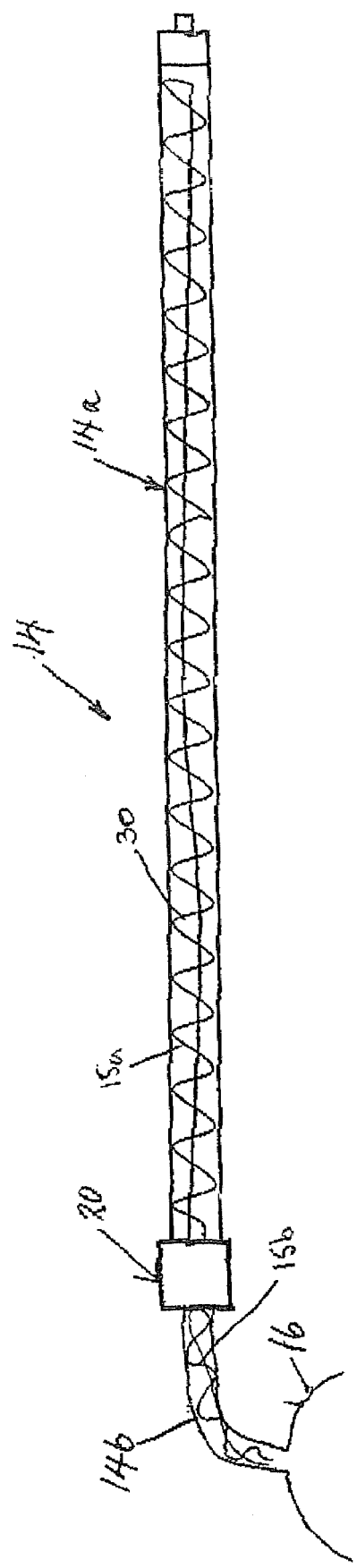
FIG. 2 is a view of the inspiratory conduit showing the preferred embodiment of connector of the present invention.

The conduit 14 is shown in FIG. 2 wherein a heating element 30, such as a copper filament, is provided within the conduit 14 to help prevent condensation of the humidified gases within the conduit 14. Such condensation is due to the temperature of the walls of the conduit 14 being close to the ambient temperature, (being the temperature of the surrounding atmosphere) which is usually lower than the temperature of the humidified gases within the conduit 14. The heating element 30 effectively replaces the energy lost from the gases through conduction and convection during transit through the conduit 14. Thus the conduit heating element 30 ensures the gases delivered to the patient are at an optimal temperature and humidity.

As discussed in the prior art it is preferable that a piece of soft flexible conduit is used to connect the heated respiratory conduit to the patient interface 16. As this flexible conduit is unheated it can be prone to producing condensation thereby disrupting the temperature and humidity of the gases flowing through the flexible conduit. In order to remove the condensation and retain ease of movement of the patient interface, a heating element 30 may be added to the flexible section 14b of the conduit 14. The heated flexible section 14b is attached to the rest of the heated respiratory conduit 14a by way of a swivelling connector 20.

Furthermore, it may also be necessary to have additional contacts electrical wires extending through the conduit 14 and flexible section 14b that carry signals from sensors (for example, temperature, humidity, pressure, optical or sound sensors) to the patient interface. These additional contacts, such as known electrical wires, may be moulded into the conduit or merely extend within the conduit. In the case where no heating of the gas needed but an electrical connection extending though the conduit to the patient interface, an appropriate connection is required.

Figure 3:
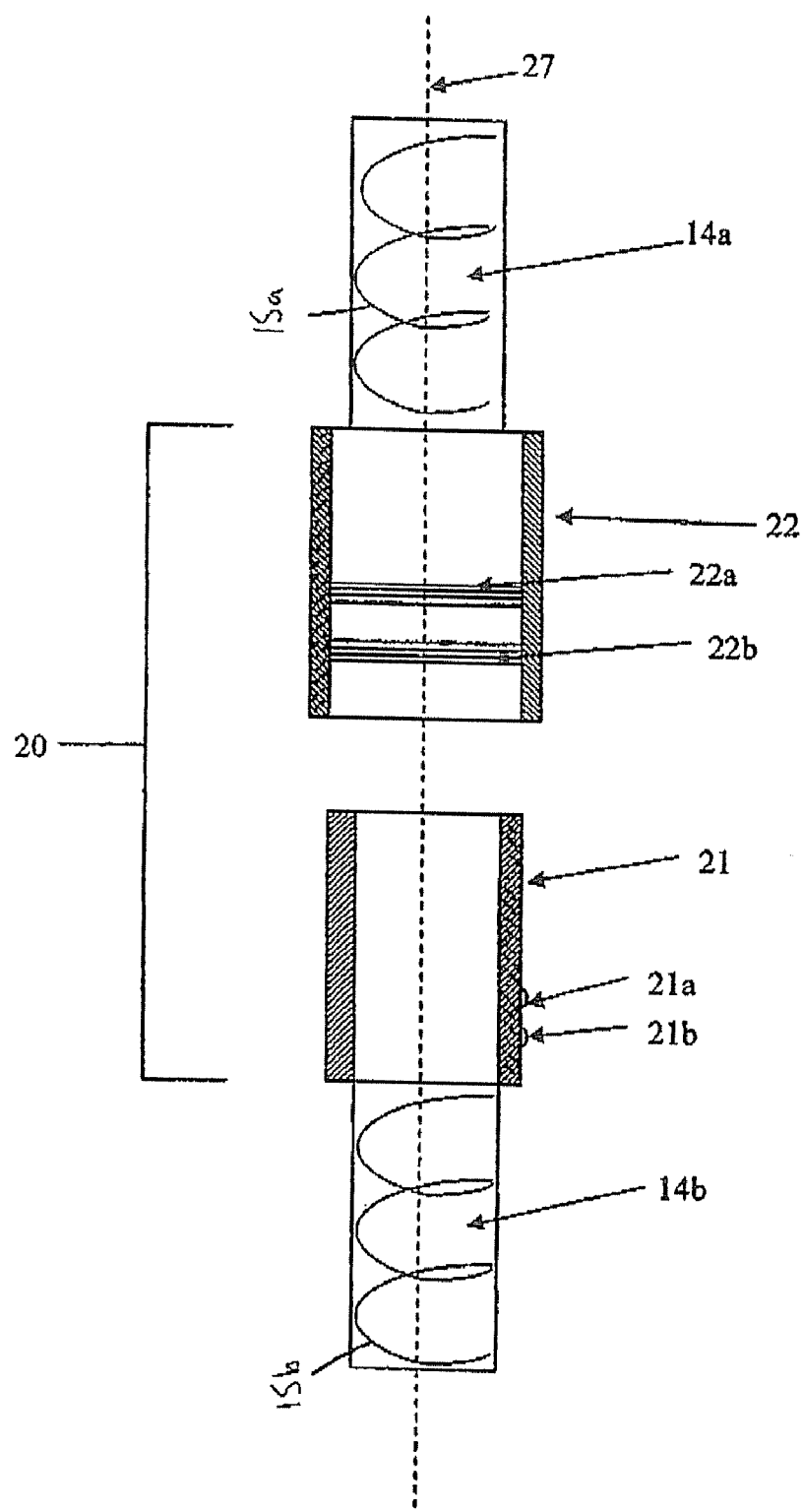
FIG. 3 is a cross-sectional view of the preferred embodiment of the connector of the present invention where the male and female portions of the connector are unconnected.

The preferred embodiment of the connector 20 of the present invention is shown in FIG. 3 and provides both electrical and gaseous connections between the conduits 14a and 14b and possibly an additional electrical connection to the interface connectors to one end of the conduit 14b. On one end of the conduit 14b is the male portion 21 of the connector 20. On the corresponding end of the conduit 14a is the female portion 22 of the connector 20.

Note in the description below the electrical contacts are described as being a heating element 30, electrical wire, extending through the conduits, 14a, 14b. It is intended that along with or instead of the heating element additional electrical contacts may be extend although not described specifically.

The male connector portion 21 is preferably manufactured from a thermoplastic material and is preferably over moulded, by way of injection moulding, over the end of the conduit 14b. The heating element 30 within the conduit 14b has two terminals or contacts 21a, 21b on the exterior of the connector 21. The contacts 21a, 21b are positive and negative (respectively) and are made from an electrically conductive material, for example, copper. The contacts 21a, 21b project outwards from the exterior of the connector 21. The contacts 21a, 21b may be any shape, but preferably are circular. Again, these contacts 21a, 21b are moulded into the male connector portion 21 during manufacture.

The female connector portion 22 is also preferably manufactured from a thermoplastic material and is preferably over moulded, by way of injection moulding, over the end of the conduit 14a The heating element 30 within conduit the 14a is similarly made up of two wires, a positive and a negative wire, therefore on the female connector 22 there are two terminals or contacts 22a, 22b. The terminals 22a, 22b are positive and negative respectively and are located on the interior face of the female portion 22. The terminals 22a, 22b are shaped like a ring. The profile of the terminals 22a, 22b are such that they match the exterior profile of the contacts 21a, 21b. Again, these terminals 22a, 22b are moulded into the male connector portion 21 during manufacture.

Figure 4:
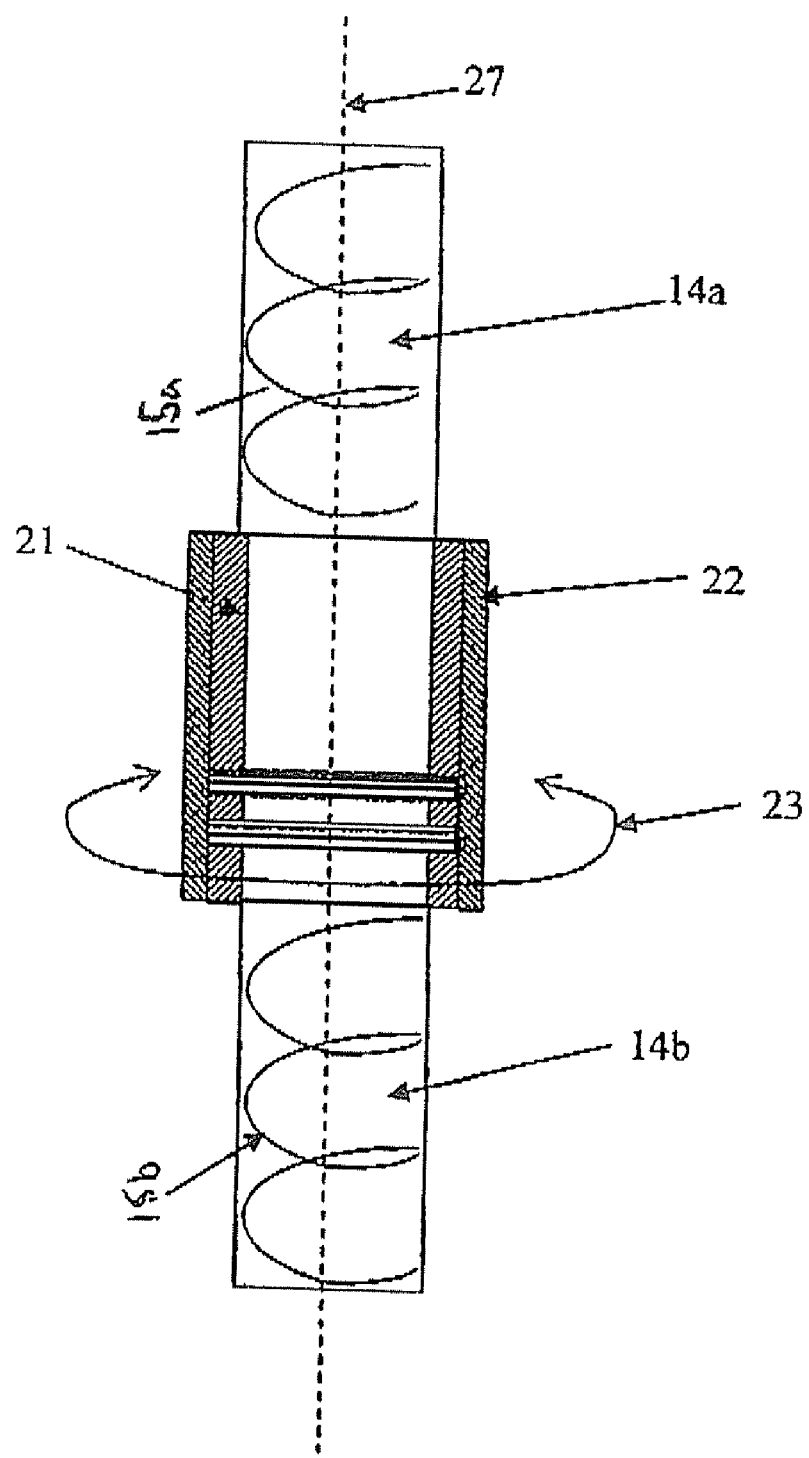
FIG. 4 is a cross-section of the preferred embodiment of the connector of FIG. 3 where the connector is in an 'in use' configuration.

When a connection is made between the male and female portions 21, 22 as shown in FIG. 4, the contacts 21a, 21b fit into or touch the terminals 22a, 22b respectively. This securely fits the connector 21 to the connector 22 and allows rotational movement 23 about the y-axis 27 without loss of either electrical or gaseous connection. This connector also allows for the flexible conduit 14b to be supplied with current to power a separate heating wire 15b in the flexible conduit 14b.

Figure 5:
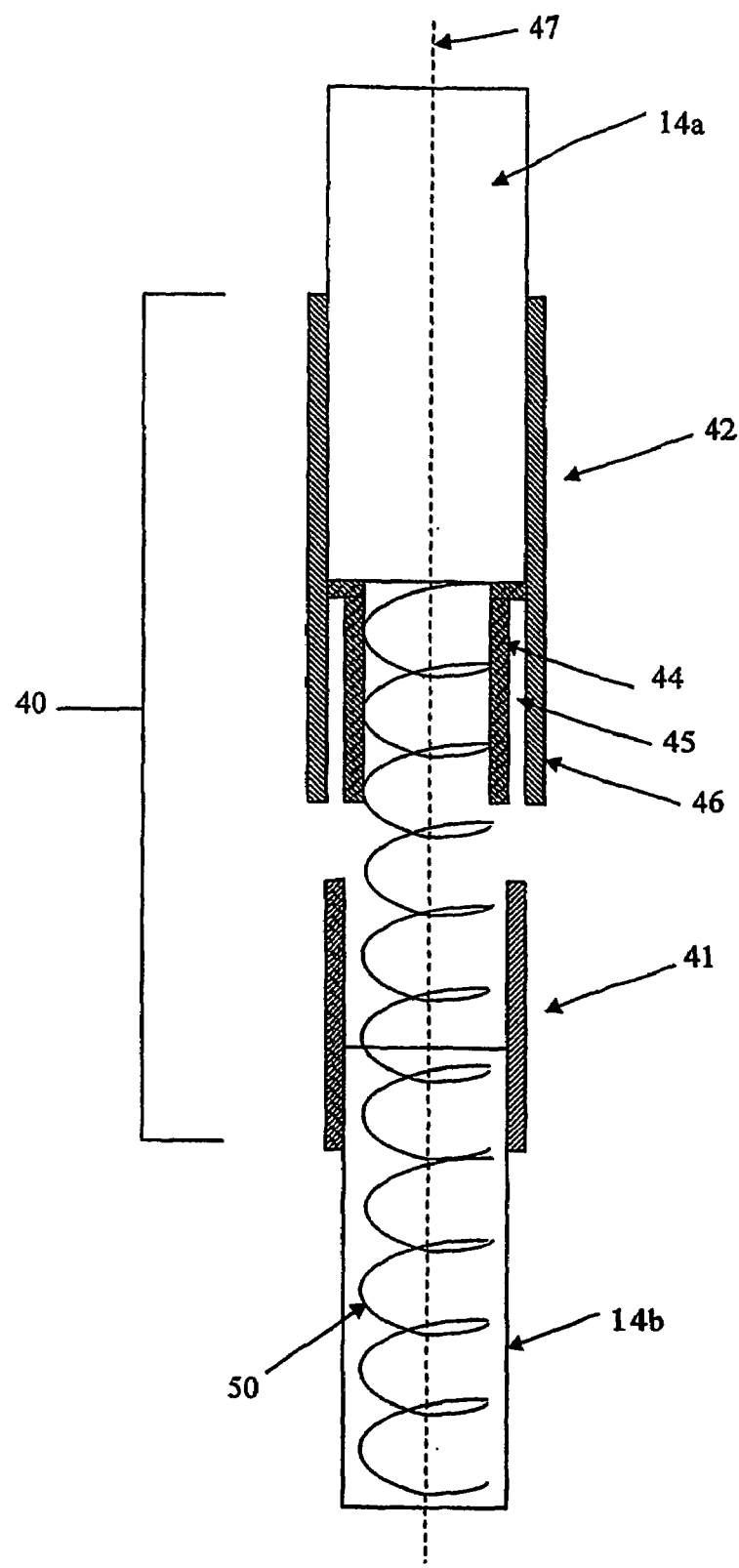
FIG. 5 is a cross-sectional view of the alternative embodiment of the connector of the present invention, where the male and female portions of the connector are unconnected.
Figure 6:
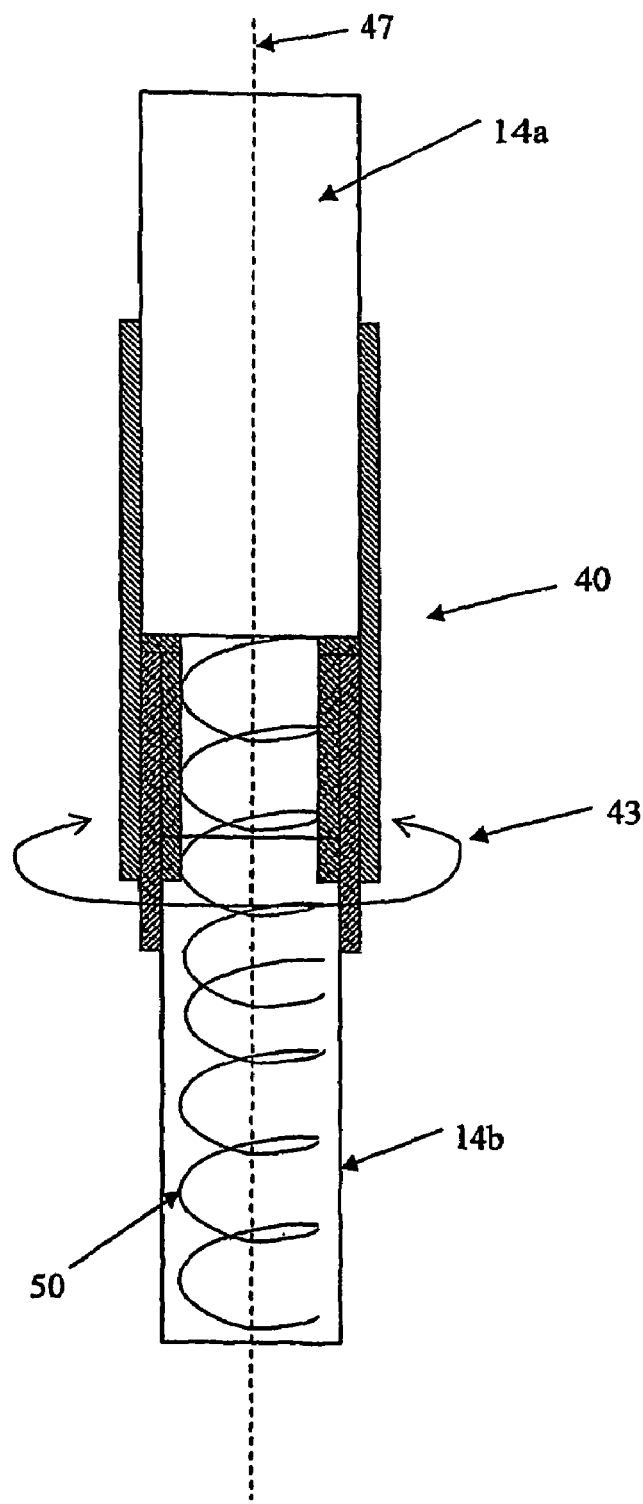
FIG. 6 is a cross-section of the alternative embodiment of the connector of FIG. 5 where the connector is in an 'in use' configuration.

The alternate embodiment of a connector of the present invention is shown in FIGS. 5 and 6. This connector 40 also provides an electrical and gaseous connection between one end of the first conduit 14a and one end of the second conduit 14b. This connection is also able to be twisted around the y-axis 47 (as indicated by arrow 43, shown in FIG. 6) without loss of connection. In FIG. 6, the male connector 41 is shown not connected to the female connector 42.

The male connector 41 is again made of a thermoplastic material and is effectively a tubular moulding formed about the end of the flexible conduit 14b. The female connector 42 is over moulded on to one end of the conduit 14a by known processes, for example by injection moulding, and is manufactured from a thermoplastic material. The end of the female connector 42 (where the male connector 41 is inserted, as shown in FIG. 5) consists of an inner tube 44 and an outer tube 46 located around the outer circumference of the inner tube 44. This creates a recess 45 between these tubes 44, 46 that is capable of receiving the male portion 41. The recess 45 is substantially the same width as the width of the male portion 41. Although not shown, the connection between the male connector 41 and female connector 42 is capable of being locked or automatically locking when connecting. A seal, for example, by a friction fit or latching is necessary to ensure no gas leakages.

In use, when the male portion 41 is inserted into the female portion 42 to form a connection, the male portion 41 can be twisted in the female portion 42 about the y-axis 47. In order to heat the conduit 14b, the heating element 50 within the heated conduit 14a may extend out from the heated conduit 14a (as shown in FIG. 6) and in use, into the flexible conduit 14b. The heating element 50 may have several embodiments. In one embodiment, the heating element 50 may be loose within the conduit 14a and simply threaded through the connector 40 into the conduit 14b. Alternately, the heating element 50 may be an integral part of the wall of the conduit 14a (as previously described) and extend out from the heated conduit 14a through the connector 40 and into the flexible conduit 14b.

In each of the embodiments described above a locking mechanism is provided between the male connectors and female connectors. For example, the connectors may fit together by way of a thread or bayonet type fitting, or by way of any one of the pneumatic locking mechanisms as described in New Zealand Patent Application Number 519374 of Fisher & Paykel Healthcare Limited.

We claim:

1. A connector for use in a system for the delivery of humidified pressurised gases to a patient, said connector adapted to couple a first conduit to a second conduit to provide a gaseous connection and an electrical connection between said first and second conduits,
    said first and second conduits including first and second electrical elements extending within, throughout or about said conduits,
    said connector comprising:
    a tubular male portion located on one end of said first conduit and having a first electrical contact on its exterior, said first electrical contact forming part of said first electrical element,
    a tubular said female portion located on one end of said second conduit and having a second electrical contact on its interior, said second electrical contact forming part of said second electrical element,
    in use, said male and female portions connected so that a gaseous connection is formed between said first and second conduits, said first electrical contact and said second electrical contact meeting when said male and female portions are connected, said male and female portions capable of being swivelled or twisted relative to one another without disrupting said gaseous connection and said electrical connection between said first and second electrical contacts.

2. A connector according to claim 1 wherein said electrical elements are heating elements capable of causing heating in at least one of said first conduit or said second conduit.

3. A connector according to claim 1 wherein said electrical elements are wires that provide power to or enable sensing at one of said first conduit or said second conduit.

4. A connector according to claim 1 wherein said electrical elements are at least one heating element and a wire to supply power to or enable sensing at at least one of said first conduit, or said second conduit.

* * * * *